(12) United States Patent
Ganem et al.

(10) Patent No.: US 6,494,910 B1
(45) Date of Patent: Dec. 17, 2002

(54) DEVICE FOR TREATING PRESBYOPIA OR OTHER OCULAR DISORDER

(75) Inventors: Stéphane Ganem, Paris (FR); Jérôme Stubler, Neuilly/Seine (FR); Gilles Bos, Sillingy (FR)

(73) Assignee: Societe Medicale de Precision S.M.P. SA, Plan-les-Quates (CH)

( * ) Notice: Subject to any disclaimer, the term of this patent is extended or adjusted under 35 U.S.C. 154(b) by 0 days.

(21) Appl. No.: 09/869,466

(22) PCT Filed: Dec. 29, 1999

(86) PCT No.: PCT/FR99/03307
§ 371 (c)(1),
(2), (4) Date: Jun. 28, 2001

(87) PCT Pub. No.: WO00/40174
PCT Pub. Date: Jul. 13, 2000

(30) Foreign Application Priority Data

Dec. 31, 1998 (FR) .............................................. 98 16723

(51) Int. Cl.[7] .................................................. A61F 2/14
(52) U.S. Cl. ...................................... 623/4.1; 625/5.12
(58) Field of Search ................................ 623/4.1, 5.11, 623/5.14, 6.11–6.14, 6.38–6.44

(56) References Cited

U.S. PATENT DOCUMENTS

| | | | |
|---|---|---|---|
| 4,214,585 A | * 7/1980 | Bailey, Jr. .................. | 606/107 |
| 5,366,499 A | * 11/1994 | Py .............................. | 623/4.1 |
| 5,766,242 A | * 6/1998 | Wong et al. ................. | 128/898 |
| 5,806,530 A | * 9/1998 | Herrick ...................... | 128/898 |
| 5,838,419 A | * 11/1998 | Holland ...................... | 351/162 |

FOREIGN PATENT DOCUMENTS

| | | |
|---|---|---|
| DE | 298 01 281 U1 | 3/1998 |
| EP | 0 544 948 A1 | 6/1993 |
| EP | 0 732 090 A1 | 9/1996 |
| WO | WO 94/02084 | 2/1994 |
| WO | WO 95/03755 | 2/1995 |
| WO | WO 99/17684 | 4/1999 |
| WO | WO 99/17691 | 4/1999 |

\* cited by examiner

Primary Examiner—Corrine McDermott
Assistant Examiner—Hieu Phan
(74) Attorney, Agent, or Firm—Weingarten, Schurgin, Gagnebin & Lebovici LLP

(57) ABSTRACT

The invention concerns a device for treating presbyopia or other ocular disorders related to any eye accommodation defect. The device (20) includes a piece (22) shaped as a ring portion with an axis of revolution and first (22a) and second (22b) edges offset along radial directions and along the direction of said axis of revolution. The first edge (22a) is disposed to rest, over at least part of its length, on part of the eye internal wall and the second part (22b) is capable of being pressed against a median zone (18c) of zonules of the crystalline lens (18). In this way a displacement of the median zone of said zonules is obtained. This displacement enables them to cause the deformation of the crystalline lens (14) under the effects of stimulation applied to the zonules.

16 Claims, 2 Drawing Sheets

DEVICE FOR TREATING PRESBYOPIA OR OTHER OCULAR DISORDER

The present invention has for its object a device intended to be placed in the eye to treat presbyopia or other ocular disorders related to an eye accommodation defect.

In order to understand more readily the problem to be solved, accompanying FIG. 1 shows a half-view of an eye in vertical section. This Figure shows the cornea 1, the internal wall of the eye 4 with its ciliary body 6 and the iris 8 which defines the pupil 9 of the eye. This Figure also shows the sulcus which constitutes a groove between the ciliary body 6 and the iris 8 as well as the crystalline lens 14 with its capsular sac 16. The crystalline lens 14, or, more precisely, its capsular sac 16 is connected to the wall 4 of the eye by an assembly of muscles called zonules constituted by fibrils. These fibrils have one end 18a which is connected to the periphery of the capsular sac 16 and another end which is embedded in the ciliary body 6. When the eye is in a normal state, the controlled contractions of the zonules 18 provoke modification of the radii of curvature of the crystalline lens 14, thus allowing accommodation of the eye as a function of the distance at which the object to be looked at is located.

It has been demonstrated that the ageing of the eye tended to produce an increase in the outer dameter of the crystalline lens. As a result, the zonules become "too long" and are "relaxed" and the impulses applied to the fibrils of the zonules no longer enable the latter to act on the crystalline lens to provoke accommodation.

It has also been demonstrated that it is the traction exerted on the capsular sac by the zonules which makes it possible to increase the optical power of the crystalline lens, by provoking a reduction of the radius of curvature of its posterior face.

An object of the present invention is to provide a device adapted to be implanted in the eye, which makes it possible to render the zonules active again in order to allow accommodation despite the increase in the diameter of the crystalline lens.

To attain that object, according to the invention, the device for treating presbyopia or other ocular disorder related to an eye accommodation defect is characterized in that it comprises a piece having substantially the shape of at least a ring portion with an axis of revolution and a first edge disposed on a circle of diameter D1 included between 12.5 and 13.5 mm and a second edge disposed on a circle of diameter D2 included between 9.5 and 10.5 mm, said edges being offset in the direction of said axis of revolution by a length h included between 0.5 and 2.5 mm, said first edge being designed to rest, over at least part of its length, on part of the internal wall of the eye and said second edge being capable of being pressed against a median zone of the zonules of the crystalline lens, whereby is obtained a displacement of said median zone of said zonules stressing them and enabling them to cause the deformation of the crystalline lens under the effect of stimulations applied to said zonules.

It will be understood that the ring or ring portion positioned inside the eye rests by its outer edge in the zone of the ciliary sulcus while its other inner edge applied against the median zone of the zonules provokes the rearward displacement of this median zone of the zonules as well as of the crystalline lens. This displacement makes it possible to obtain a new stressing of the zonules which will thus be rendered active again when the fibrils which constitute them are excited.

According to a first embodiment of the invention, the ring is closed and in that case it is made of a supple biocompatible material in order to allow insertion of the ring inside the eye. According to a second embodiment of the invention, the ring is open and, in that case, it may be made of a rigid biocompatible material such as for example PMMA.

In the present text, it must be specified that "supple material" is understood to mean materials currently used for manufacturing intraocular implants in particular and which are typically constituted by polyHEMAs or by silicon gels. The term "rigid material" must be understood to mean translucent biocompatible materials presenting a low coefficient of elasticity and of which the most well known is PMMA.

Other characteristics and advantages of the invention will appear more readily on reading the following description of embodiments of the invention given by way of non-limiting examples. The description is made with reference to the accompanying Figures, in which:

FIG. 1, already described, shows half of an eye, in vertical section.

FIG. 2 shows the positioning of the device for treating presbyopia, in the eye.

FIG. 3 schematically illustrates the mode of action of the device for treating presbyopia FIG. 4 is a front view of an embodiment of the device for treating presbyopia.

Figure 5:
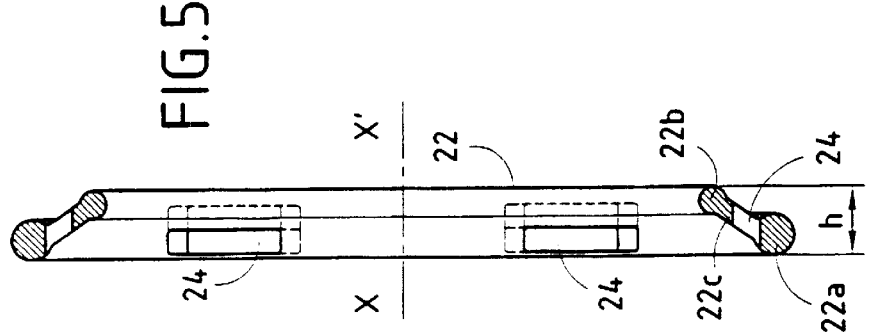
FIG. 5 is a side view in section along line V—V of the device of FIG. 4.
Figure 4:
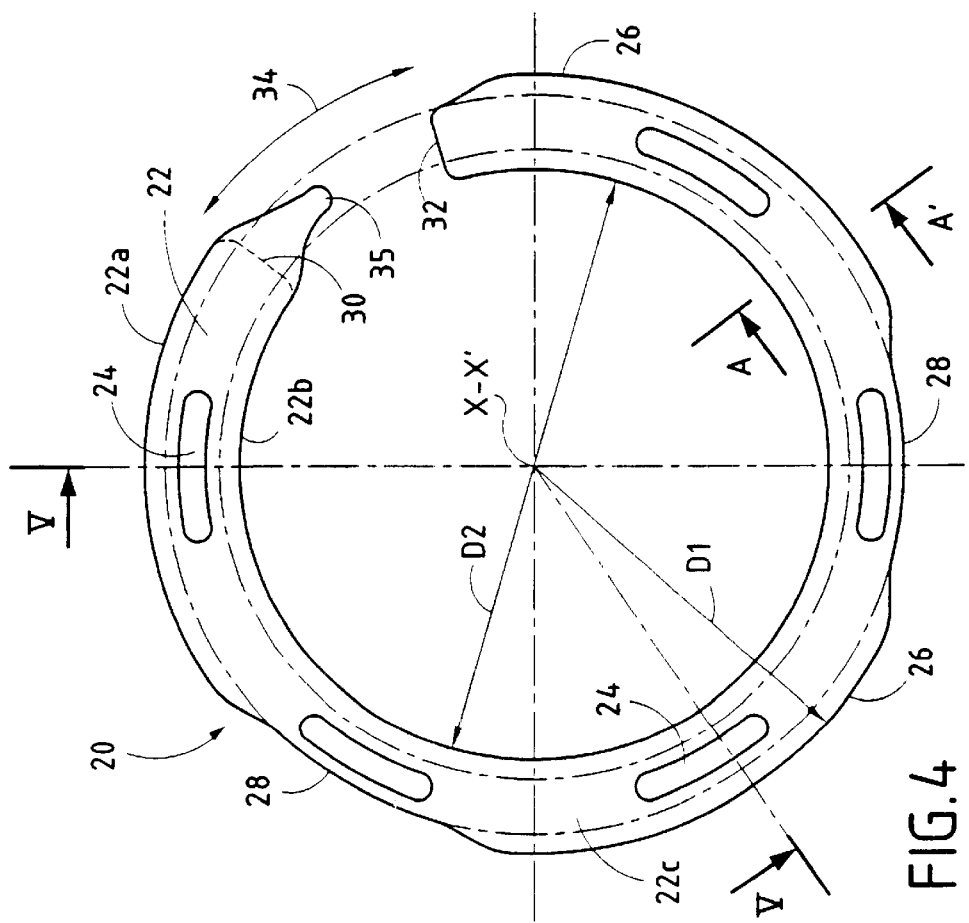

Referring firstly to FIGS. 4 and 5, an embodiment of the device for treating presbyopia will be described. This device referenced 20 presents the general shape of a ring or a ring portion 22 comprising an outer edge 22a and an inner edge 22b. The ring 22 may be closed or present an opening as apparent in FIG. 4. The edges 22a end 22b may present a rounded shape and are joined together by a planar portion 22c.

Figure 1:
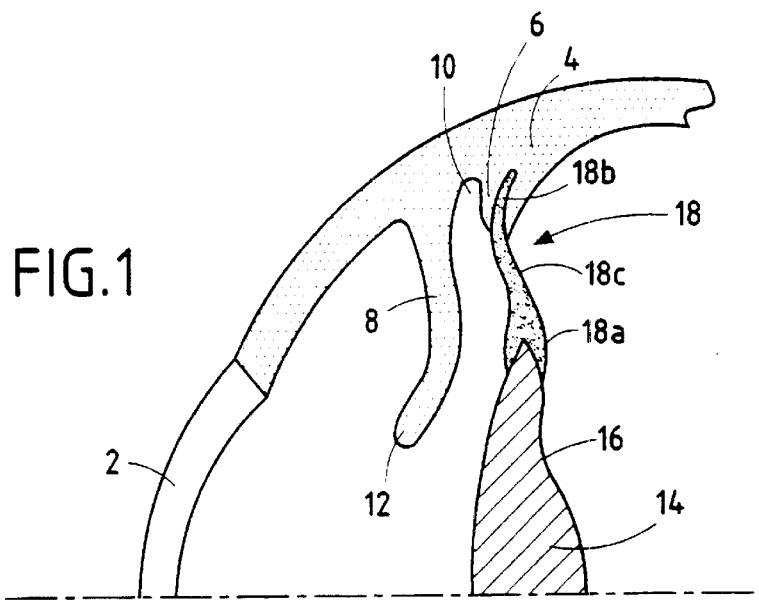
Figure 2:
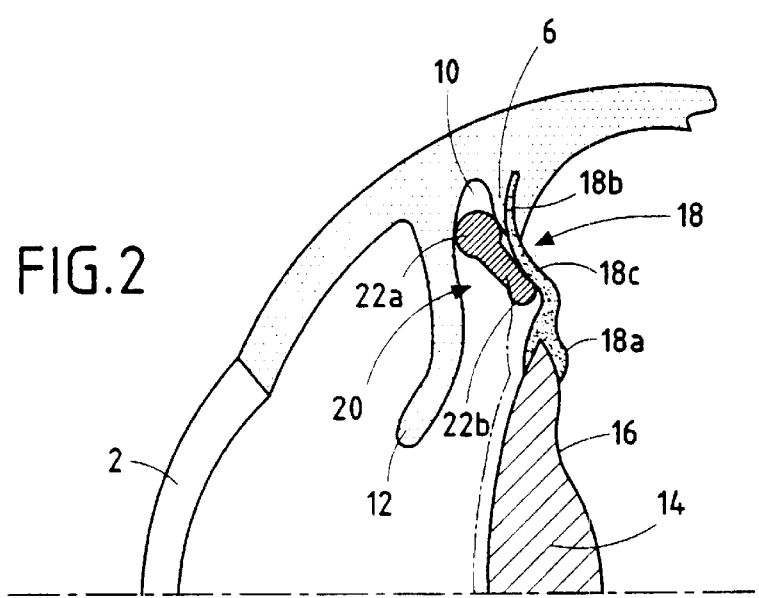

FIG. 2 shows a treatment device 20 placed in the eye. As shown in this Figure, the outer edge 22a rests on the wall of the eye in the zone of the ciliary sulcus 10, while the inner edge 22b is applied against the median zone 18 of the zonules 18c so as to provoke displacement of this median zone as will be explained hereinafter.

Figure 5A:
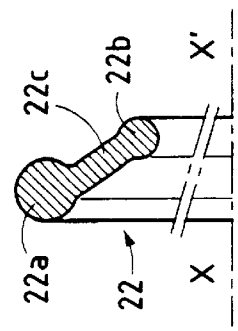
FIG. 5A is a partial view in section along line A—A of FIG. 5.

The intermediate zone 22c of the ring or ring portion 22 must present sufficient dimensions for the inner edge 22b to effectively allow displacement of the median zone of the zonules. That is to say that the intermediate part 22c must present a sufficient mechanical strength for the distance between the outer and inner edges to remain constant when the ring is placed in position. These dimensions will, of course, depend on the material used for obtaining the desired mechanical strength. As shown in FIG. 2 or FIG. 5a, the ring 22 presents the general shape of a portion of truncated cone, such that the outer edge 22a is disposed on a circle of diameter D1, the inner edge 22b is disposed on a circle of diameter D2 smaller than D1, and that an offset h in the direction of the optical axis X-X' exists between the outer edge 22a and the inner edge 22b.

When the treatment device is placed in position in the eye, the edge 22a constitutes an anterior edge and the edge 22b a posterior edge.

Figure 3:
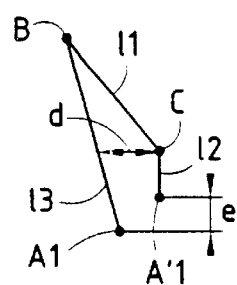

FIG. 3 schematically shows the effect produced by the positioning of the treatment device 20 in the eye. In this Figure, B symbolizes a fictitious point of anchorage of the zonules in the ciliary body and A1 the point of anchorage of the zonules on the periphery of the capsular sac, 13 representing the distance between points B and A1 in the absence of the treatment device. By the action of the inner edge 22b on the median zone of the zonules, the fibrils constituting the zonules see their median part C displaced by a distance d towards the rear of the eye. Such displacement of the median zone C also provokes a displacement of point A1 which is in that case called $A'_1$. The displacement in the direction of the optical axis is equal to d and a displacement in directions orthogonal to the optical axis, i.e. in the radial directions of the crystalline lens, of value e, is obtained. It will be understood that such antero-posterior displacements provoke a certain rearward displacement of the whole of the crystalline lens and allow stressing of the zonules thanks to the displacement of the median zone. Everything occurs, with respect to the crystalline lens, as if the length of the zonules had been reduced by the length e. The increase of the diameter of the crystalline lens is thus compensated.

Referring again to FIGS. 4 and 5, a preferred embodiment of the treatment device 20 will be described in greater detail. The central part of the ring 20, referenced 22c, is preferably pierced with orifices 24 regularly spaced angularly and allowing the free circulation of the aqueous humor on all sides of the device in the anterior chamber. Similarly, the outer edge 22a is preferably constituted by arcs of circle such as 26 separated by recessed regions 28. The arcs of circle 26 are regularly distributed angularly. Consequently, the rest on the inner wall of the eye is effected solely by the sectors corresponding to the arcs of circle 26, the recessed portions 28 also allowing free passage of the aqueous humor.

In the case of the embodiment of FIG. 4, the treatment device 22 is simply constituted by a ring portion limited by ends 30 and 32 leaving an opening 34. In order to facilitate insertion of the ring in the eye by the incision made in the wall thereof, the end 30 may preferably be provided with an elongated extension 34.

In the case of the treatment device 20 being constituted by only a ring portion presenting the opening 34, it is possible to make this ring of a rigid material such as PMMA. The opening 34 may preferably be included between 30 and 120 degrees, thus ensuring a sufficient action on the zonules.

It is also possible to use a treatment device constituted by a closed ring and therefore not having opening 34. In that case, it is, of course, necessary that this ring be made of a supple material of the type marketed under the Trademark Hydrogel to allow the ring to bend around a diameter with a view to introducing the device 20 in the eye through an incision of relatively reduced dimensions.

In the embodiment described by way of example, the outer diameter D1 is equal to 13.1 mm and the inner diameter D2 is equal to 9.9 mm. More generally, the diameter. D1 is preferably included between 12.5 and 13.5 mm and the diameter D2 included between 9.5 and 10.5 mm.

The offset h between the two edges in the direction of the optical axis is equal to 1.25 mm in order to obtain a sufficient displacement of the median zone of the zonules. More generally, this offset h is included between 0.5 and 2.5 mm and preferably between 1 and 1.5 mm.

The angle of aperture 34 between the two ends of the ring is 35 degrees. More generally, it is included between 30 and 120 degrees.

Finally, as shown in FIGS. 5 and 5a, the respectively outer and inner edges of the ring 20 preferably present a rounded shape. The corresponding radius of curvature is preferably included between 0.20 and 0.35 mm in order to avoid any lesion of the zonules or of the inner wall of the eye.

What is claimed is:

1. Device for treating presbyopia or other ocular disorder related to an eye accommodation defect, characterized in that it comprises a piece having substantially the shape of at least a ring portion having the general shape of a truncated cone with an axis of revolution and a first edge disposed on a circle of diameter D1 included between 12.5 and 13.5 mm and a second edge disposed on a circle of diameter D2 included between 9.5 and 10.5 mm, said edges being offset in the direction of said axis of revolution by a length h included between 0.5 and 2.5 mm, said first edge being designed to rest, over at least part of its length, on part of the internal wall of the eye and said second edge being capable of being pressed against a median zone of the zonules of the crystalline lens, said first and second edges being joined together by a central part which presents a sufficient mechanical strength for the second edge to provoke a displacement of said median zone of said zonules stressing them and enabling them to cause the deformation of the crystalline lens under the effect of stimulations applied to said zonules.

2. Device according to claim 1, characterized in that the offset in the direction of the axis of revolution, between the first edge and the second edge, is included between 1.0 mm and 1.5 mm.

3. Device according to claim 2, characterized in that:

said first edge is constituted by arcs of circle separated by recessed portions;

said arcs of circle forming said first edge are regularly distributed angularly with respect to said axis of revolution;

said piece is in the form of one of an open ring terminating in two ends, and a closed ring.

4. Device according to claim 1, characterized in that said first edge is constituted by arcs of circle separated by recessed portions.

5. Device according to claim 4, characterized in that said arcs of circle forming said first edge are regularly distributed angularly with respect to said axis of revolution.

6. Device according to claim 5, characterized in that:

said piece is in the form of a ring portion terminating in two ends, the angle at the centre between these ends being included between 30 and 120 degrees;

one of the two ends of the piece in the form of ring portion is extended by an elongated portion in order to facilitate positioning of the ring in the eye;

it is made of one of a rigid biocompatible material, which is made of PMMA and a supple biocompatible material.

7. Device according to claim 1, characterized in that said piece is in the form of an open ring terminating in two ends.

8. Device according to claim 1, characterized in that said piece is in the form of a closed ring.

9. Device according to claim 1, characterized in that said piece is in the form of a ring portion terminating in two ends, the angle at the centre between these ends being included between 30 and 120 degrees.

10. Device according to claim 9, characterized in that one of the two ends of the piece in the form of ring portion is extended by an elongated portion in order to facilitate positioning of the ring in the eye.

11. Device according to claim 9, characterized in that it is made of a rigid biocompatible material.

12. Device according to claim 11, characterized in that it is made of PMMA.

13. Device according to claim 1, characterized in that it is made of a supple biocompatible material.

14. Device according to claim 13, characterized in that the edges of said ring are rounded and the ring is in the form of a portion of truncated cone.

15. Device according to claim 1, characterized in that the edges of said ring are rounded.

16. Device according to claim 1, characterized in that the ring is in the form of a portion of truncated cone.

* * * * *

UNITED STATES PATENT AND TRADEMARK OFFICE
CERTIFICATE OF CORRECTION

PATENT NO. : 6,494,910 B1
DATED : December 17, 2002
INVENTOR(S) : Stéphane Ganem et al.

It is certified that error appears in the above-identified patent and that said Letters Patent is hereby corrected as shown below:

Title page,
Item [75], "Sillingy" should read -- La Balme de Sillingy --

Column 1,
Line 3, insert -- BACKGROUND OF THE INVENTION --;
After line 31, insert -- BRIEF SUMMARY OF THE INVENTION --;

Column 2,
After line 8, insert -- BRIEF DESCRIPTION OF THE SEVERAL VIEWS OF THE DRAWING --; and
After line 23, insert -- DETAILED DESCRIPTION OF THE INVENTION --.

Signed and Sealed this

Eleventh Day of May, 2004

JON W. DUDAS
*Acting Director of the United States Patent and Trademark Office*